US009545441B2

(12) United States Patent
Simard

(10) Patent No.: US 9,545,441 B2
(45) Date of Patent: Jan. 17, 2017

(54) TREATMENT OF DIABETES

(71) Applicant: XBiotech, Inc., Vancouver (CA)

(72) Inventor: John Simard, Austin, TX (US)

(73) Assignee: XBiotech, Inc., Vancouver (CA)

(*) Notice: Subject to any disclaimer, the term of this patent is extended or adjusted under 35 U.S.C. 154(b) by 375 days.

(21) Appl. No.: 14/030,561

(22) Filed: Sep. 18, 2013

(65) Prior Publication Data

US 2014/0086933 A1  Mar. 27, 2014

Related U.S. Application Data

(60) Provisional application No. 61/702,362, filed on Sep. 18, 2012, provisional application No. 61/762,479, filed on Feb. 8, 2013.

(51) Int. Cl.
*A61K 39/395* (2006.01)
*A61K 39/00* (2006.01)
*C07K 16/24* (2006.01)

(52) U.S. Cl.
CPC ......... *A61K 39/3955* (2013.01); *C07K 16/245* (2013.01); *A61K 2039/505* (2013.01); *A61K 2039/54* (2013.01); *A61K 2039/545* (2013.01)

(58) Field of Classification Search
CPC .............. C07K 14/245; A61K 39/3955; A61K 2039/505; A61K 2039/54; A61K 2039/545
See application file for complete search history.

(56) References Cited

U.S. PATENT DOCUMENTS

| 4,634,664 | A | 1/1987 | Oestberg |
|---|---|---|---|
| 4,965,198 | A | 10/1990 | Yamasaki et al. |
| 5,034,316 | A | 7/1991 | Weisbart et al. |
| 5,168,062 | A | 12/1992 | Stinski |
| 5,231,024 | A | 7/1993 | Moeller et al. |
| 5,585,089 | A | 12/1996 | Queen et al. |
| 5,654,407 | A | 8/1997 | Boyle et al. |
| 5,693,762 | A | 12/1997 | Queen et al. |
| 5,792,838 | A | 8/1998 | Smith et al. |
| 5,795,967 | A | 8/1998 | Aggarwal et al. |
| 5,932,188 | A | 8/1999 | Snow et al. |
| 5,959,085 | A | 9/1999 | Garrone et al. |
| 6,090,382 | A | 7/2000 | Salfeld et al. |
| 6,140,470 | A | 10/2000 | Garen et al. |
| 6,623,736 | B2 | 9/2003 | Tobinick |
| 7,718,674 | B2 | 5/2010 | Aberg |
| 8,398,966 | B2 | 3/2013 | Wu |
| 2003/0026806 | A1 | 2/2003 | Witte et al. |
| 2003/0040617 | A9 | 2/2003 | Rosen et al. |
| 2003/0175832 | A1 | 9/2003 | Marton |
| 2003/0232054 | A1 | 12/2003 | Tang et al. |
| 2004/0097712 | A1 | 5/2004 | Varnum |
| 2004/0185514 | A1 | 9/2004 | Frostegard |
| 2005/0054019 | A1 | 3/2005 | Michaud et al. |
| 2005/0147603 | A1 | 7/2005 | Smith et al. |
| 2005/0276807 | A1 | 12/2005 | Skurkovich |
| 2006/0127407 | A1 | 6/2006 | Chen |
| 2006/0159775 | A1 | 7/2006 | McGrath |
| 2007/0071675 | A1 | 3/2007 | Wu et al. |
| 2008/0050310 | A1 | 2/2008 | Ebens, Jr. et al. |
| 2009/0123415 | A1 | 5/2009 | Simard |
| 2009/0191149 | A1 | 7/2009 | Simard |
| 2009/0258070 | A1 | 10/2009 | Burnier |
| 2009/0291081 | A1 | 11/2009 | Hsieh |
| 2009/0298096 | A1 | 12/2009 | Simard |
| 2010/0040574 | A1 | 2/2010 | Simard |
| 2010/0047239 | A1 | 2/2010 | Wu |
| 2010/0068212 | A1 | 3/2010 | Simard |
| 2010/0221179 | A1 | 9/2010 | Hsieh |
| 2011/0008282 | A1 | 1/2011 | Simard |
| 2011/0142761 | A1 | 6/2011 | Wu et al. |
| 2011/0311547 | A1 | 12/2011 | Simard |
| 2012/0015384 | A1 | 1/2012 | Simard |
| 2012/0045444 | A1 | 2/2012 | Simard |
| 2012/0231012 | A1 | 9/2012 | Simard |
| 2012/0251548 | A1 | 10/2012 | Simard |
| 2013/0039921 | A1 | 2/2013 | Simard |
| 2013/0078258 | A1 | 3/2013 | Simard |
| 2013/0195877 | A1 | 8/2013 | Simard |
| 2013/0287788 | A1 | 10/2013 | Simard |

FOREIGN PATENT DOCUMENTS

| AU | 2007202323 | 5/2007 |
|---|---|---|
| CA | 2426384 | 4/2003 |
| EP | 0267611 | 5/1993 |
| EP | 0659766 | 6/1995 |
| JP | 2004285057 | 4/2004 |
| WO | 9635719 | 11/1996 |

(Continued)

OTHER PUBLICATIONS

Larsen C.M. et al. Interleukin-1-receptor antagonist is type 2 diabetes mellitus. New England Journal of Medicine, 2007, vol. 356, p. 1517-1526.*

Larsen, C.M., et al. Sustained effects of interleukin-1 receptor antagonist treatment in type 2 diabetes. Diabetes Care, 2009, vol. 32, p. 1663-1668.*

Levetan, C. Oral antidiabetic agents in type 2 diabetes. Current Medical Research and Opinion, 2007, vol. 23, No. 4, p. 945-952.*

Sawai, H, et al. Interleukin-1alpha enhances the aggressive behavior of pancreatic cancer cells by regulating the alpha6beta1-integrin and urokinase plasminogen activator receptor expresison. BMC Cell Biology, 2006, vol. 7, No, 8, p. 1-13.*

Svenson M, et al. Cytokine vaccination: neutralising IL-1alpha autoantibodies induced by immunisiation with homologous IL-1alpha. Journal of Immunological Methods, 2000, vol. 236, No. 1-2), p. 1-8.*

Shirakawa F., et al. Autocrine stimulation of interleukin 1 alpha in the growth of adult human T-cell leukemia cells. Cancer Research, 1989, vol. 49, p. 1143-1147.*

Interleukin 1 alpha is a marker of endothelial cellular senescent. Immunity and Ageing, 2006, vol. 3, No. 4, p. 1-6.*

Niki, Y, et al. Membrane-associated IL-1 contributes to chronic synovitis and cartilage destruction in human IL-1 alpha transgenic mice. J. Immunology, 2004, vol. 172, No. 1, p. 577-584.*

(Continued)

*Primary Examiner* — Robert Landsman
*Assistant Examiner* — Bruce D Hissong
(74) *Attorney, Agent, or Firm* — Stanley A. Kim

(57) ABSTRACT

Glycated hemoglobin (HbA1c) levels and other characteristics of diabetes are reduced by administering to a human subject a pharmaceutical composition that includes a pharmaceutically acceptable carrier and a therapeutically effective amount of an agent that selectively binds IL-1α.

9 Claims, 3 Drawing Sheets

(56) References Cited

FOREIGN PATENT DOCUMENTS

| WO | 0233094 | 4/2002 |
|---|---|---|
| WO | 2004100987 | 11/2004 |
| WO | 2006001967 | 1/2006 |
| WO | 2007015128 | 2/2007 |
| WO | 2007039552 | 4/2007 |
| WO | 2007120828 | 10/2007 |
| WO | 2007132338 | 11/2007 |
| WO | 2007135546 | 11/2007 |
| WO | 9006371 | 9/2009 |
| WO | 2009148575 | 12/2009 |
| WO | 2010030979 | 3/2010 |
| WO | 2010087972 | 8/2010 |
| WO | 2011159976 | 12/2011 |
| WO | 2012027324 | 3/2012 |
| WO | 2012135812 | 3/2012 |
| WO | 2013043973 | 3/2013 |
| WO | 2014055541 | 4/2014 |
| WO | 2014055544 | 4/2014 |

OTHER PUBLICATIONS van Asseldonk, E.J.P., et al. One week treatment with the IL-1 receptor antagonist anakinra leads to a sustained improvement in insulin sensitivity in insulin resistant patients with type 1 diabetes mellitus. Clinical Immunology, 2015, vol. 160, p. 155-162.*
Marques-Deak, Andrea et al: "Measurement of cytokines in sweat patches and plasma in healthy women: Validation in a controlled study," Journal of Immunological Methods, vol. 315, 2006: 99-109.
Sigma Life Science: "Gel Filtration Chromatography," no date; cited in Office Action of U.S. Appl. No. 13/225,029 on Jun. 19, 2014.
Janik, John E. et al: "Interleukin 1alpha increases serum leptin concentrations in humans," Journal of Clinical Endocrinology and Metabolism, vol. 92, No. 9, 1997: 3084-3086.
Kurokawa, Ichiro et al: "New developments in our understanding of acne pathogenesis and treatment," Experimental Dermatology, vol. 18, 2009:821-832.
Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.
Oriuchi, Noboru et al: "Current status of cancer therapy with radiolabeled monoclonal antibody," Annals of Nuclear Medicine, vol. 19, No. 5, 2005:355-365.
Boselli, Joseph et al: Fibronectin: Its relationshp to basement membranes, Light Microscopic Studies, Cell.Res., vol. 5, 1981:391-404.
Clinical Trial Review: Acne; <<http://jddonline.com/articles/dermatology/S1545961612P0780X/1>>, last visited on Oct. 16, 2014.
Hoge, E.A. et al: "Broad spectrum of cytokine abnormalities in panic disorder and posttraumatic stress disorder," Depression and Anxiety, vol. 26, No. 5, May 2009:447-455; Abstract only.
Saitta, Peter et al: "An update on the presence of psychiatric comorbidities in acne patients, part 2: depression, anxiety, and suicide," Cutis, vol. 88, 2011:92-97.
Mach, Francois: "Toward new therapeutic strategies against neointimal formation in restenosis," Arterioscler Thromb Vasc Biol, vol. 20, 2000:1699-1700.
Morton, Allison, C. et al: "Interleukin-1 receptor antagonist alters the response to vessel wall injury in a porcine coronary artery model," Cardiovascular Research, vol. 68, 2005: 493-501.
Heyderman, R.S. et al: "Modulation of the endothelial procoagulant response to lipoploysaccharide and tumour necrosis factor-alpha in-vitro: The effects of dexamethasone, pentoxifylline, iloprost and a polyclonal anti-human IL-1alpha antibody," Inflarrinn Res, vol. 44, 1995:275-280.
Joosten, M. et al: "Amelioration of established collagen-induced arthritis (CIA) with anti-IL-1," Agents Actions. vol. 41, Special Conference Issue, 1994:C174-C176.

Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.
Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.
Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.
Svenson, M. et al., IgG Autoantibodies against Interleuking 1alpha in sera of normal individuals, Scand. J. Immunol., 1989, vol. 29:489-492.
McHale, Julie F. et al., TNF-alpha and IL- sequentially induce endothelial ICAM-1 and VCAM-1 expression in MRL/Ipr lupus-prone mice, The American Association of Immunologists, 1999, vol. 163:3993-4000.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011.
XBiotech, Inc. Pressrelease: "XBiotech Files Investigational New Drug (IND) Application with the FDA for the treatment of Chronic Myelogenous Leukemia," Evaluate, Nov. 22, 2010.
Fujii, Masakazu et al.: "A case of advanced gastric cancer with carcinomatous ascites successfully treated with intraperitoneal administration of CDDP and TS-1," Japanese Journal of Gastroenterological Surgery, 2006, vol. 39:189-195.
Yamada, Takayuki et al.: "Growth Dependency of a new human pancreatic cancer cell line, YAPC, on autocrine interleukin-1 alpha stimulation," Int. J. Cancer, 1998, vol. 76:141-147.
El-Osta, Hazem et al.: "Successful treatment of Castleman's Disease with Interleukin-1 receptor antagonist (Anakinra)," Molecular Cancer Therapy, 2010, vol. 9:1485-1488.
Dinarello, Charles A. et al: "Treating inflammation by blocking interleukin-1 in a broad spectrum of diseases," Nature Reviews Drug Discovery, 2012, vol. 11:633-652.
Bendtzen, Klaus et al., High-Avidity Autoantibodies to Cytokines, Trends Immunology Today, May 1998, vol. 19, No. 5 209.
Bendtzen, Klaus et al., Detection of Autoantibodies to Cytokines, Molecular Biotechnology, 2000, vol. 14.
Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.
Dinarello, Charles A., Modalities for reducing interleukin 1 activity in disease, TiPS, May 1993, vol. 14:155-159.
Dinarello, Charles A. et al., Anticytokine strategies in the treatment of the systemic inflammatory response syndrome, The Journal of the American Medical Association, Apr. 1993, vol. 269, No. 14:1829-1835.
Dinarello, Charles A., Biologic basis for interleukin-1 in disease, Blood, Mar. 1996, vol. 87, No. 6:2095-2147.
Dinarello, Charles A., Therapeutic strategies to reduce IL-1 activity in treating local and system inflammation, Current Opinion in Pharmacology, 2004, vol. 4:378-385.
Larrick, James W. et al., Prospects for the therapeutic use of human monoclonal antibodies, Journal of Biological Response Modifiers, 1986, vol. 5:379-393.
Garrone, P. et al., Generation and characterization of a human monoclonal autoantibody that acts as a high affinity interleukin-1alpha specific inhibitor, Molecular Immunology, 1996, vol. 33. No. 78:649-658.
Griffiths, Andrew D. et al., Human anti-self antibodies with high specificity from phage display libraries, the EMBO Journal, 1993, vol. 12, No. 2:725-734.

(56) References Cited

OTHER PUBLICATIONS

Satoh, H. et al., Characterization of anti-IL-1alpha autoantibodies in the sera from healthy humans, Immunopharmacology, 1994, vol. 27:107-118.
Hansen, M. B. et al., Sex- and age-dependency of IgG autoantibodies against IL-1alpha in healthy humans, European Journal of Clinical Investigation, 1994, vol. 24:212:218.
Jouvenne, P. et al., High levels of neutralizing autoantibodies against IL-1alpha are associated with a better prognosis in chronic polyarthritis: a follow-up study, Scand. J. Immunol., 1997, vol. 46:413-418.
Lindqvist, E. et al., Prognostic laboratory markers of joint damage in rheumatoid arthritis, Ann Rheum Dis, 2005, vol. 64:196-201.
Ogushi, F. et al., Autoantibodies to IL-1alpha in sera from rapidly progressive idiopathic pulmonary fibrosis, The Journal of Medical Investigation, 2001, vol. 48:181-189.
Ross, Christian, et al., High avidity IFN-neutralizing antibodies in pharmaceutically prepared human IgG, J. Clin. Invest., May 1995, vol. 95:1974-1978.
Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.
Suzuki, Hiroshi et al., Demonstration of Neutralizing Autoantibodies against Il-1alpha IN sera from patients with rheumatoid arthritis, The Journal of Immunology, Oct. 1, 1990, vol. 145, No. 7:2140-2146.
Svenson, M. et al., IgG Autoantibodies against Interleuking lalpha in sera of normal individuals, Scand. J. Immunol., 1989, vol. 29:489-492.
Svenson, M. et al., Binding of Cytokines to Pharmaceutically Prepared Human Immunoglobulin, J. Clin. Invest., Nov. 1993, vol. 92:2533-2539.
Svenson, M. et al., Effects of human anti-IL-1alpha autoantibodies on receptor binding and biological activities of IL-1 alpha, Cytokine, Mar. 1992, vol. 4, No. 2:125-133.
Svenson, M. et al., Distribution and characterization of autoantibodies to interleukin 1 alpha in normal human sera, Scand. J. Immunol., 1990, vol. 32:695-701.
Svenson, M. et al., Antibody to granulocyte-macrophage colony-stimulating factor is a dominant anti-cytokine activity in human IgG preparations, Blood, Mar. 1998, vol. 91, No. 6:2054-2061.
Svenson, M. et al., Cytokine vaccination: neutralising IL-1alpha autoantibodies induced by immunisation with homologous IL-1alpha, Journal of immunological methods, 2000, vol. 236, 1-8.
Waehre et al., Increased expression of interleukin-1 in coronary artery disease with downregulatory effects of HMG-CoA reductase inhibitors, <<circ.ahajournals.org>>, downloaded on Jan. 15, 2008:1966-1972.
Clinton Steven K. et al., Interleukin-1 gene expression in rabbit vascular tissue in vivo, American Journal of Pathology, Apr. 1991, vol. 138, No. 4:1005-1014.
Von Der Thusen, Jan H., et al., Interleukins in atherosclerosis: Molecular pathways and therapeutic potential, Pharmacol Rev, 2003, vol. 55, No. 1:133-166.
Kasahara, T. et al., Preparation and characterization of polyclonal and monoclonal antibodies against human interleukin 1 alpha (IL 1alpha), The Journal of Immunology, Mar. 1987, vol. 138, No. 6:1804-1812.
Merhi-Soussi, F. et al., Interleukin-1 plays a major role in vascular inflammation and atherosclerosis in male apoliprotein E-knockout mice, Cardiovacular Research, 2006, vol. 66:583-593.
Ross, C. et al., Increased in vivo antibody activity against interferon alpha, interleuking-1alpha, and interleukin-6 after high-dose Ig therapy, Blood, Sep. 1997, vol. 90, No. 6:2376-2380.
Ito, R. et al., Interleukin 1alpha acts as an autocrine growth stimulator for human gastric carcinoma cells, Cancer Research, Sep. 1993, vol. 53:4102-4106.

Shirakawa, F. et al., Autocrine stimulation of interleukin 1alpha in the growth of adult human T-cell leukemia cells, Cancer Research, Mar. 1989, vol. 49:1143-1147.
Apte, Ron N., et al., Effects of micro-environment- and malignant cell-derived interleukin-1 in carcinogenesis, tumour invasiveness and tumour-host interactions, European Journal of Cancer, 2006, vol. 42:751-759.
Dinarello, Charles A., The role of interleukin-1 in disease, The New England Journal of Medicine, 1993, vol. 328, No. 2:106-113.
Wake, R. et al., Gender differences in ischemic heart disease, Recent Patents on Cardiovascular Drug Discovery, 2009, vol. 4:234-240.
Mariotti, Massimo et al., Iterleukin 1 alpha is a marker of endothelial cellular senescent, Immunity & Ageing, Research, Apr. 2006, vol. 3, No. 4:1-6.
Niki, Yasuo et al., Membrane-associated IL-1 contributes to Chronic Synovitis and cartilage destruction in human IL-1alpha transgenic mice, the Journal of Immunology, 2004, vol. 172:577-584.
McHale, Julie F. et al., TNF-alpha and IL-sequentially induce endothelial ICAM-1 and VCAM-1 expression in MRL/Ipr lupus-prone mice, The American Association of Immunologists, 1999, vol. 163:3993-4000.
Sandborg, Christy L. et al., Modulation of IL-1alpha, IL-1 beta, and 25K Mr Non-IL-1 activity released by human mononuclear cells, Journal of Leukocyte Biology, 1989, vol. 46:417-427.
GenBank entry AY510107.1, Homosapiens 9F11 monoclonal IgM antibody light chain mRNA, complete cds, 2005 (retrieved from the Internet on Apr. 23, 2010, <http://www.ncbi.nlm.nih.gov/nuccore/41388185>.
Sunahara, N. et al., Differential determination of recombinant hum interleukin-1 alpha and its deamidated derivative by two sandwhich enzyme immunoassays using monoclonal antibodies. Comparison with a polyclonal antibody-based competitive enzyme immunoassay., J Immunol Methods, 1989, vol. 119:75-82 (Abstract only).
Miossec, P., Anti-interleukin 1alpha autoantibodies, Ann Rheum Dis, 2002, vol. 61:577-579.
Horai, R. et al., Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J. Exp. Med, 1998, vol. 187, No. 9:1463-1475.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Braddock, M. et al., Therapeutic potential of targeting IL-1 and IL-18 in inflammation, Expert Opin. Biol. Ther., 2004, vol. 4, No. 6:8476-860.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
Janeway, C.A., Jr. et al, The induction, measurement, and manipulation of the immune response, ImmunoBiology, the Immune System in Health and Disease, 1997, Third Edition.
Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.
Chamberlain, R.S. et al., Innovations and strategies for the development of anticancer vaccines, Exp. Opin. Pharmacother., 2000, vol. 1(4)603-614.
Jefferis, Roy: "Antibody therapeutics: isotype and glycoform selection," Expert Opin. Biol. Ther. (2007) 7 (9):1401-1413.
Salfeld, J.G.: "Isotype selection in antibody engineering," Nature Biotechnology (2007), vol. 25, No. 12:1369-1372.
Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.

(56) References Cited

OTHER PUBLICATIONS

Buchan, G. et al: "Interleukin-1 and tumour necrosis factor mRNA expression in rheumatoid arthritis: prolonged production of IL-1alpha," Clin. Exp. Immunol. (1988), vol. 73:449-455.

Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.

Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.

Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.

Yanni, G. et al: "Intramuscular gold decreases cytokine expression and macrophage numbers in the rheumatoid synovial membrane," Annals of the Rheumatic Diseases, 1994, vol. 53:315-322.

Dekker, S.K. et al: "Characterization of interleukin-1alpha-induced melanoma cell motility: inhibition by type I and type II receptor-blocking monoclonal antibodies," Melanoma Research, 1997, vol. 7:223-230.

Kleiman, et al: "Invasion assays," Current Protocols in Cell Biology, 2001, 12.2.1-12.2.5.

Sawai, H. et al: "Interleukin-1alpha enhances the aggressive behavior of pancreatic cancer cells by regulating the alpha 6 beta 1-integrin and urokinase plasminogen activator receptor expression," BMC Cell Biology, 2006, vol. 7:8:1-13.

Lewis, Anne M. et al: "Interleukin-I and cancer progression: the emerging role of interleukin-I receptor antagonist as a novel therapeutic agent in cancer treatment," Journal of Translational Medicine, 2006, vol. 4:1-12.

Li, X. al: X et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.

Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.

Voronov, E. et al: "IL-1 is required for tumor invasiveness and angiogenesis," PNAS, 2003, vol. 100, No. 5:2645-2650.

Uefuji, K. et al: "Increased expression of interleukin-1alpha and cyclooxygenase-2 in human gastric cancer: a possible role in tumor progression," 2005, Anticancer Research, vol. 25:3225-3230.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

Mizutani, H.: "Endogenous neutralizing anti-Il-1alpha antibodies in inflammatory skin diseases: possible natural inhibitor nhibitor for over expressed epidermal IL-1," 1999, Journal of Dermatological Science, vol. 20:63-71.

Skrzeczynska, J. et al.: "CD14+CD16+ Monocytes in the Course of Sepsis in Neonates and Small Children: Monitoring and Functional Studies," 2002, Scand. J. Immunol., vol. 55:629-638.

Zhu, Y. et al., "The Clinical study about interleukin-1 and tumor necrosis factor Alpha in hepatocirrhosis," Chinese Journal of Clinical Hepatology, 2001, vol. 17, Issue 4: 233-234.

* cited by examiner

TREATMENT OF DIABETES

CROSS-REFERENCE TO RELATED APPLICATIONS

This application claims priority from U.S. patent application Ser. No. 61/702,362 filed on Sep. 18, 2012 and U.S. patent application Ser. No. 61/762,479 filed on Feb. 8, 2013.

STATEMENT AS TO FEDERALLY SPONSORED RESEARCH

Not applicable.

FIELD OF THE INVENTION

The invention relates generally to the fields of medicine, endocrinology, and immunology. More particularly, the invention relates to the use of agents which specifically bind interleukin-1α(IL-1α) to treat diabetes.

BACKGROUND

The cardinal symptom of diabetes mellitus (DM or diabetes) is high blood sugar. This condition can result from either the lack of insulin production (type 1 DM or T1D) or the loss of sensitivity to insulin (type 2 DM or T2D). Other forms of diabetes include gestational diabetes, congenital diabetes from genetic defects of insulin secretion, cystic fibrosis-related diabetes, and steroid-induced diabetes. All of these can be treated with insulin and T2D can also be controlled with other medications such as hypoglycemic agents. Unfortunately, however, neither T1D nor T2D can be cured. Uncontrolled diabetes can lead to several acute and chronic problems including hypoglycemia, diabetic ketoacidosis, nonketotic hyperosmolar coma, cardiovascular disease, chronic renal failure, and diabetic retinopathy. The better diabetes is controlled, the lesser the chance a person has of developing these problems.

SUMMARY

The invention is based on the discovery that an agent that specifically binds IL-1α is useful for treating diabetes.

Accordingly, the invention features a method of treating diabetes in a human subject. Treatment of diabetes can involve improving beta cell function; increasing insulin and/or C-peptide levels; improving proinsulin to insulin ratios; and/or decreasing HbA1c levels. The method can include the step of administering to the subject a pharmaceutical composition including a pharmaceutically acceptable carrier and an amount of an agent that selectively binds IL-1α effective to treat diabetes in the subject. The agent can be an anti-IL-1α antibody, and the anti-IL-1α antibody can be a monoclonal or polyclonal antibody. The monoclonal antibody can be an IgG1, can include a complementarity determining region of MABp1 (see U.S. patent application Ser. No. 13/225,029 for a description of this antibody), and/or can be MABp1.

The subject can be one concomitantly being treated with an oral hypoglycemic medication and/or one with an HbA1c of between 7 and 10% prior to the step of administering to the subject a pharmaceutical composition. The step administering to the subject a pharmaceutical composition is repeated at least two times (e.g., at least 2, 3, 4, 5, 6, 7, 8, 9, 10 or more times), until an improvement in beta cell function; increasing insulin and/or C-peptide levels; proinsulin to insulin ratios; and/or HbA1c levels is observed.

The step administering to the subject a pharmaceutical composition can be performed by intravenous administration or another suitable method such as subcutaneous or intramuscular administration.

Another aspect of the invention includes the use of an agent that selectively binds to IL-1α to treat diabetes in a human subject or the use of an agent that selectively binds IL-1α in preparation of medicament for treating diabetes in a human subject. The agent can be an anti-IL-1α antibody and the anti-IL-1α antibody can be a monoclonal or polyclonal antibody. The monoclonal antibody can be an IgG1, can include a complementarity determining region of MABp1, and/or can be MABp1. The subject can be one concomitantly being treated with an oral hypoglycemic medication; one with an HbA1c of between 7 and 10% prior to the step of administering to the subject a pharmaceutical composition; and/or one with abnormal insulin and/or C-peptide levels; or abnormal proinsulin to insulin ratios.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27$^{th}$ Edition, Lippincott, Williams & Wilkins, 2000.

As used herein, an "antibody" or "Ab" is an immunoglobulin (Ig), a solution of identical or heterogeneous Igs, or a mixture of Igs. An "Ab" can also refer to fragments and engineered versions of Igs such as Fab, Fab', and F(ab')$_2$ fragments; and scFv's, heteroconjugate Abs, and similar artificial molecules that employ Ig-derived CDRs to impart antigen specificity. A "monoclonal antibody" or "mAb" is an Ab expressed by one clonal B cell line or a population of Ab molecules that contains only one species of an antigen binding site capable of immunoreacting with a particular epitope of a particular antigen. A "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule. An Ab that "selectively binds" a first molecule specifically binds the first molecule at a first epitope but does not specifically bind other molecules that do not have the first epitope. For example, an Ab which selectively binds IL-1α specifically binds an epitope on IL-1 alpha but does not specifically bind IL-1 beta (which does not have the epitope).

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All patents, patent applications, and publications mentioned herein are incorporated by reference in their entirety. In the case of conflict, the present specification, including definitions will control. In addition, the particular embodiments discussed below are illustrative only and not intended to be limiting.

DETAILED DESCRIPTION

Figure 1:
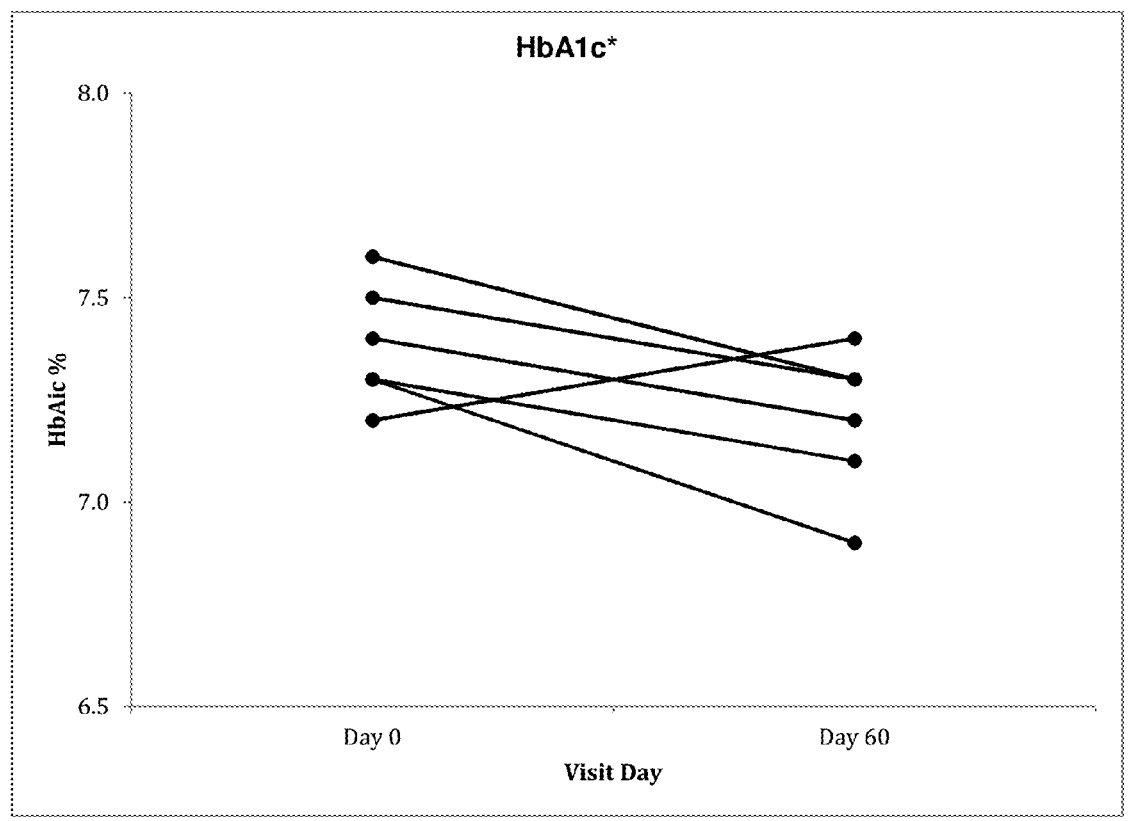
FIG. 1 is a graph showing improvement of HbA1c in diabetic subjects following treatment with an anti-IL-1α monoclonal antibody.
Figure 2:
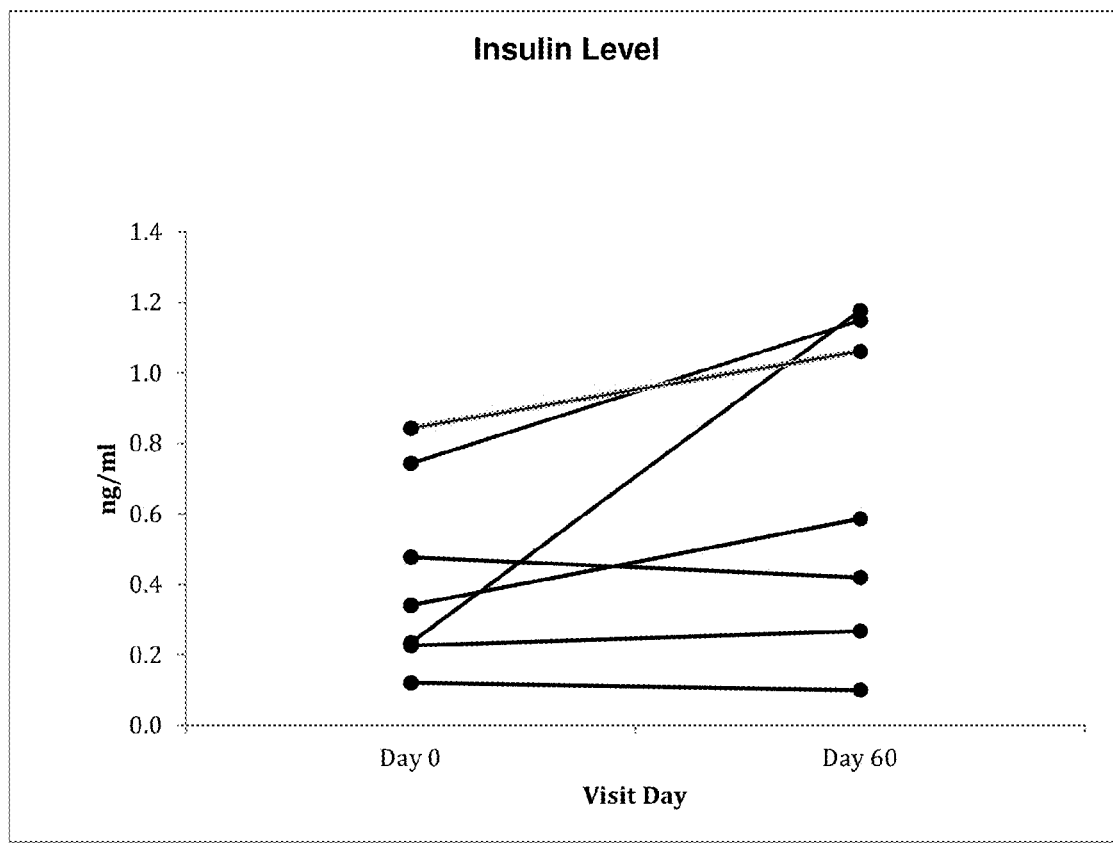
FIG. 2 is a graph showing improvement of insulin levels in diabetic subjects following treatment with an anti-IL-1α monoclonal antibody.
Figure 3:
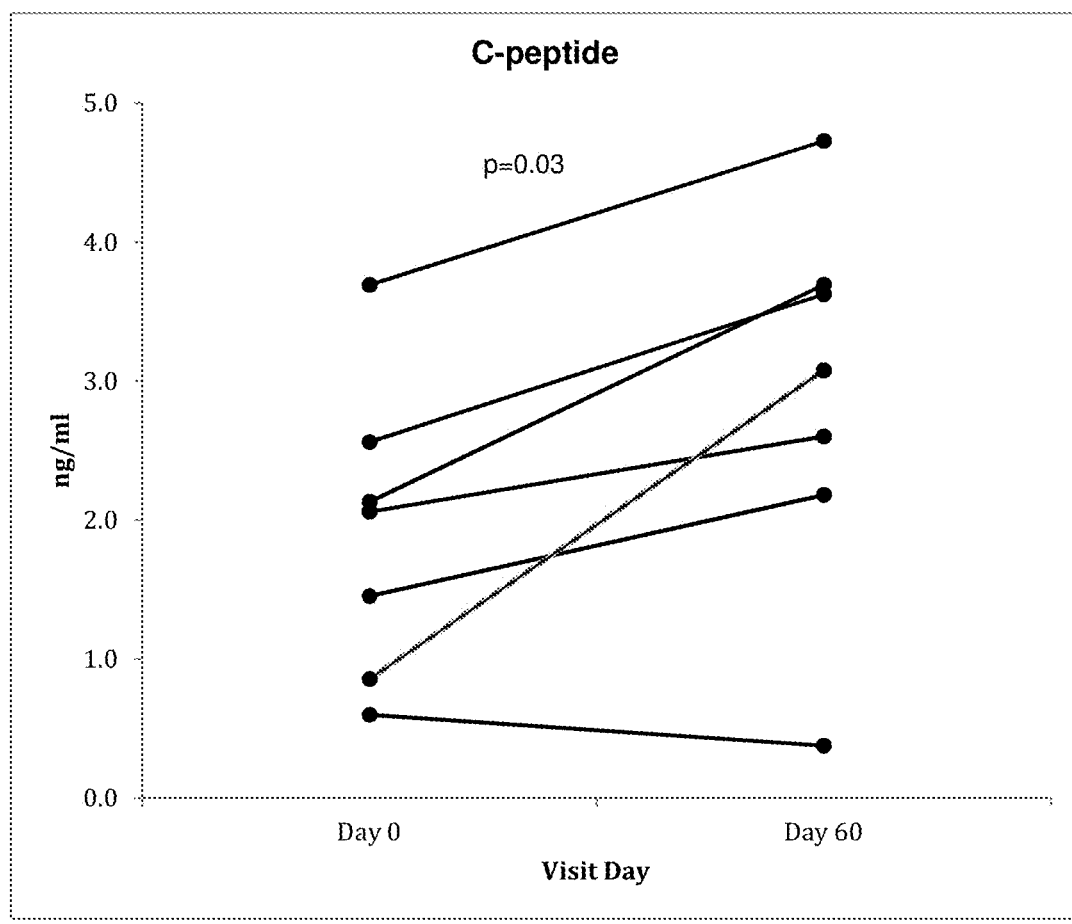
FIG. 3 is a graph showing improvement of C-peptide levels in diabetic subjects following treatment with an anti-IL-1α monoclonal antibody.

The invention encompasses compositions and methods for treating diabetes in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein. Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, 49$^{th}$ Edition, McGraw-Hill Medical, 2010; and Fauci et al., Harrison's Principles of Internal Medicine, 17$^{th}$ Edition, McGraw-Hill Professional, 2008. Methods in endocrinology and treatment of diabetes are described in J. Jameson, Harrison's Endocrinology Second Ed., McGraw-Hill Professional, 2010.

Treatment of Diabetes

The compositions and methods described herein are useful for treating diabetes (e.g., T1D or T2D) in a diabetic mammalian subject by administering to the subject a pharmaceutical composition including an amount of an anti-IL-1α Ab effective to improve at least one characteristic of diabetes [e.g., hyperglycemia, HbA1c levels, pancreatic beta cell function (e.g., as measured by serum insulin, proinsulin to insulin ratios, or C-peptide levels), polyuria, polydipsia, polyphagia, ketoacidosis, vascular disease, chronic renal failure, neuropathy, and retinopathy] in the subject. The at least one characteristic of diabetes can be improved to values within normal range or at least to levels closer to normal range than those levels before treatment. For example, HbA1c levels can be reduced to at least 5, 10, 20, 30, 40, or 50% from the subject's HbA1c level prior to the first administration of the agent, or until the HbA1c level is reduced to at least 7.2, 7.1, 7.0, 6.9, 6.8, 6.7, 6.6, 6.5, 6.4, 6.3, 6.2, 6.1, or 6.0%. As another example, C peptide and/or pro-insulin levels can be increased by at least 0.1, 0.2, 0.3, 0.4, 0.5, 0.6, 0.7, 0.8, 0.9, 1, 1.5, 2, 2.5 or more ng/ml; insulin levels can be increased by at least 0.005, 0.1, 0.2, 0.3, 0.4 or more ng/ml. Further administrations can be given to maintain glucose, HbA1c levels, pancreatic beta cell function, serum insulin, proinsulin to insulin ratios, and/or C-peptide levels within normal ranges, e.g., further administrations can be given to maintain a target HbA1c level of between 5.0-7.0%, between 5.5-6.5%, or under 7.0, 6.9, 6.8, 6.7, 6.6, 6.5, 6.4, 6.3, 6.2, 6.1, or 6.0%.

The mammalian subject might be any that suffers from diabetes including, human beings, dogs, cats, horses, cattle, sheep, goats, and pigs. Human subjects might be male, female, adults, children, seniors (65 and older), and those with other diseases. Particularly preferred subjects are those whose disease has not been adequately controlled with diet modification, oral hypoglycemic medications, and/or insulin. Subjects who have developed a human anti-human antibody response due to prior administration of therapeutic antibodies are preferred when the anti-IL-1α Ab is a true human Ab (e.g., one that is naturally expressed in a human subject) such as MABp1.

Antibodies and Other Agents that Target IL-1α

Any suitable type of Ab that specifically binds IL-1α and reduces a characteristic of diabetes such as blood glucose or HbA1c levels in a subject might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1\times10^9$ M$^{-1}$ or greater (e.g., greater than $9\times10^{10}$ M$^{-1}$, $8\times10^{10}$ M$^{-1}$, $6\times10^{10}$ M$^{-1}$, $5\times10^{10}$ M$^{-1}$, $4\times10^{10}$ M$^{-1}$, or $1\times10^{10}$ M$^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. Pat. No. 8,034,337. Other useful mAbs are those that include at least one but preferably all the CDRs of MABp1. CDRs may be determined according to known methods such as described in Ofran et al., J. Immunol., 181:6230, 2008; and *Antibody Engineering Volume* 2, 2d edition, Konterman and Dubel (eds), Springer, 2010.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, MAbs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and *E. coli* cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, mAbs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the human IL-1α mAbs might be conjugated with another molecule such as a cytotoxin. A human IL-1α specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}$S, $^{14}$C, $^{32}$P, $^{125}$I, $^{131}$I, $^{90}$Y, $^{89}$Zr, $^{201}$Tl, $^{186}$Re, $^{188}$Re, $^{57}$Cu, $^{213}$Bi, and $^{211}$At), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophosphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), *Pseudomonas* exotoxin (PE) A, PE40, abrin, saporin, pokeweed viral protein, ethidium bromide, glucocorticoid, anthrax toxin and others. See, e.g., U.S. Pat. No. 5,932,188.

While the IL-1α specific Abs described above are preferred for use in the invention, in some cases, other agents that specifically target IL-1α might be used so long as their administration leads to improvement of a characteristic of diabetes. These other agents might include vaccines that cause the production of anti-IL-1α Abs, proteins or peptides that bind IL-1α, and small organic molecules which specifically target IL-1α. Those that do not specifically bind IL-1β are preferred.

Pharmaceutical Compositions and Methods

The anti-IL-1α Ab compositions (and other agents that specifically target IL-1α) may be administered to animals or humans in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent.

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., the pancreas) by, for example, intra-pancreatic injection. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in patients as measured by the improvement in one or more symptoms of diabetes. As is well known in the medical arts, dosage for any one animal or human depends on many factors, including the subject's size, body surface area, age, the particular composition to be administered, sex, time and route of administration, general health, and other drugs being administered concurrently. Preferred doses range from about 0.1 to 5 (e.g., 0.05, 0.1, 0.15, 0.2, 0.3, 0.4, 0.5, 1, 2, 3, 4, 5, or 6) mg/kg body weight. Doses may be given repeatedly, e.g., semi-weekly, weekly, bi-weekly, tri-weekly, semi-monthly, once every three weeks, monthly, bi-monthly, or as needed (e.g., if HbA1c levels rise beyond a threshold limit).

EXAMPLES

Example 1

T2-18C3

The MABp1 molecule described in U.S. patent application Ser. No. 13/225,029 (filed Sep. 2, 2011) consists of 1332 amino acids and the primary glycoform has a molecular weight of approximately 148.1 kilodaltons. T2-18C3, is a sterile injectable liquid formulation of 15 mg/mL MABp1 in a stabilizing isotonic buffer (pH 6.4). Each 10-mL serum vial contains 10 mL of the formulation, and is sealed with a 20-mm grey bromobutyl stopper and flip-off aluminum seal. The exact composition of the bulk drug product is shown below:

Composition of T2-18C3 Drug Product

| Ingredient | Grade | Manufacturer | Concentration |
|---|---|---|---|
| MABp1 antibody | GMP | XBiotech USA Inc | 15 mg/mL |
| trehalose dihydrate | GMP, High purity, Low endotoxin | Ferro-Pfanstiehl | 60 mg/mL |
| sodium phosphate dibasic | GMP, EP, USP, JP | J T Baker (USA) | 12 mg/mL |
| citric acid monohydrate | GMP, EP, USP, BP | J T Baker (USA) | 2 mg/mL |
| polysorbate 80 | GMP, EP, NF, JP | J T Baker (USA) | 0.2 mg/mL |
| sterile water for injection | GMP, EP, USP | Microbix (Canada) | q.s. |

The product is diluted in a 100-mL bag of normal saline prior to infusion. After priming the infusion set lines, the delivery pumps are programmed to deliver 100 mL of the diluted drug product over a 1-hour period, with the subject being monitored for signs of an infusion reaction.

Example 2

Treatment of Diabetics with an Anti-IL-1α Monoclonal Antibody

Seven subjects between 18 to 70 years of age with type 2 diabetes mellitus (HbA1c level between 7.0% and 10.0%) were enrolled in the study. The median body mass index (BMI) 32 kg/m$^2$, 71% were male, median duration of type 2 diabetes was 9 years. All 7 subjects had a history of hypertension and 2 (29%) patients had coronary artery disease and dyslipidemia.

Subjects were dosed with 1.25 mg/kg of MABp1 (T2-18C3) delivered intravenously every two weeks for a total of four doses (Days 0, 14, 28, and 42). The average HbA1c level was 7.6±0.6 (median 7.4) % at baseline. On day 60, a median reduction of 0.20 absolute percentage points in HbA1c level was observed. Five of 7 (71%) patients experienced a net reduction in HbA1c on day 60; the absolute value of HbA1c decrease was 0.26±0.09 percentage points. At day 60, beta-cell function increased from day 0. Significant change in Pro-insulin (0.16 to 0.30, p=0.031), and C-peptide (0.21 to 0.31, p=0.03) values were reported, while a modest improvement in fasting insulin was observed (0.34 to 0.59).

Most subjects had very low baseline CRP and the overall CRP level did not show significant change during the study period. However, in patients who had CRP levels≥3 mg/L (n=3) at baseline, a median reduction of 27% was observed on day 60. No increase in body weight and BMI was observed. At day 60 a modest 0.6% decrease in weight and 0.2% reduction in BMI occurred (p=0.38 and 0.8 respectively). Serum lipids showed an improving trend. Total cholesterol, LDL, HDL, and triglyceride levels improved during the study period (median change −15 mg/dL, −8 mg/dL, +3 mg/dL, and −4 mg/dL respectively). Platelet counts and their aggregation were assessed on the study visits. A small increase in the platelet count was reported during the study period. Median platelet count was 290× $10^9$/L at baseline and 306×$10^9$/L at day 60. Aggregation in platelet-rich plasma (PRP) under the effect of different agonists, such as ADP, Collagen, Ristocetin, Arachidonic Acid, was examined using Light transmission aggregometry (LTA) with the use of an APACT (automated platelet aggregation coagulation tracer) 4004 aggregometer (Labor, Munich, Germany). No significant difference was observed across the visit days.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating diabetes in a human subject, the method comprising the step of repeatedly administering to the subject a pharmaceutical composition comprising a pharmaceutically acceptable carrier and an anti-interleukin-1 alpha (IL-1α) antibody until the level of glycated hemoglobin (HbA1c) in the subject is decreased.

2. The method of claim 1, wherein the anti-IL-1α antibody is a monoclonal antibody.

3. The method of claim 2, wherein the monoclonal antibody is an IgG1.

4. The method of claim 2, wherein the monoclonal antibody comprises a complementarity determining region of MABp1.

5. The method of claim 2, wherein the monoclonal antibody is MABp1.

6. The method of claim 1, wherein the subject is concomitantly being treated with an oral hypoglycemic medication.

7. The method of claim 1, wherein the subject has an HbA1c of between 7 and 10% prior to the step of administering to the subject a pharmaceutical composition.

8. The method of claim 1, wherein the step administering to the subject a pharmaceutical composition is repeated at least four times.

9. The method of claim 1, wherein the step administering to the subject a pharmaceutical composition is performed by intravenous administration.

* * * * *